(12) United States Patent
Kain et al.

(10) Patent No.: US 11,634,746 B2
(45) Date of Patent: *Apr. 25, 2023

(54) PORTABLE GENETIC DETECTION AND ANALYSIS SYSTEM AND METHOD

(71) Applicant: Illumina, Inc., San Diego, CA (US)

(72) Inventors: Robert C. Kain, San Diego, CA (US); Min-Jui Richard Shen, Poway, CA (US); John A. Moon, San Diego, CA (US); Helmy A. Eltoukhy, Woodside, CA (US)

(73) Assignee: Illumina, Inc., San Diego, CA (US)

( * ) Notice: Subject to any disclaimer, the term of this patent is extended or adjusted under 35 U.S.C. 154(b) by 296 days.

This patent is subject to a terminal disclaimer.

(21) Appl. No.: 16/540,769

(22) Filed: Aug. 14, 2019

(65) Prior Publication Data

US 2019/0367965 A1  Dec. 5, 2019

Related U.S. Application Data (63) Continuation of application No. 15/209,351, filed on Jul. 13, 2016, now Pat. No. 10,428,367, which is a
(Continued)

(51) Int. Cl.
*C12Q 1/68* (2018.01)
*C12Q 1/6837* (2018.01)
(Continued)

(52) U.S. Cl.
CPC .......... *C12Q 1/68* (2013.01); *B01L 3/502715* (2013.01); *C12Q 1/6837* (2013.01);
(Continued)

(58) Field of Classification Search
CPC ...... C12Q 1/68; C12Q 1/6837; C12Q 1/6869; B01L 3/502715; B01L 3/5027;
(Continued)

(56) References Cited

U.S. PATENT DOCUMENTS 5,599,675 A   2/1997  Brenner
5,641,658 A   6/1997  Adams et al.
(Continued)

FOREIGN PATENT DOCUMENTS

WO   WO 89/10977   11/1989
WO   WO 91/06678    5/1991
(Continued)

OTHER PUBLICATIONS

Bains et al., "A Novel Method for Nucleic Acid Sequence Determination", Journal of Theoretical Biology 135(3), 303-7 (1988).
(Continued)

*Primary Examiner* — Benjamin R Whatley
*Assistant Examiner* — Curtis A Thompson
(74) *Attorney, Agent, or Firm* — Fletcher Yoder, PC (57) ABSTRACT

A portable detector is disclosed for detecting certain analytes of interest, such as genetic material (e.g., nucleic acids). The detector includes a reading component for the detection of the analytes, and control circuitry for controlling operation of the reading component. Processing circuitry may be included to perform both primary analysis of acquired data, and where desired, secondary analysis. Where desired, some or all of the computationally intensive tasks may be off-loaded to enhance the portability and speed of the device. The device may incorporate various types of interface, technologies for reading and analysis, positioning system interfaces, and so forth. A number of exemplary use cases and methods are also disclosed.

13 Claims, 5 Drawing Sheets

Related U.S. Application Data continuation of application No. 13/790,623, filed on Mar. 8, 2013, now abandoned.

(60) Provisional application No. 61/622,773, filed on Apr. 11, 2012.

(51) Int. Cl.
| | | |
|---|---|---|
| C12Q 1/6869 | (2018.01) | |
| G01N 33/487 | (2006.01) | |
| B01L 3/00 | (2006.01) | |
| G01N 35/00 | (2006.01) | |

(52) U.S. Cl.
CPC ....... *C12Q 1/6869* (2013.01); *G01N 33/4875* (2013.01); *G01N 33/48792* (2013.01); *B01L 3/5027* (2013.01); *B01L 2200/10* (2013.01); *B01L 2300/023* (2013.01); *B01L 2300/024* (2013.01); *B01L 2300/027* (2013.01); *B01L 2300/0636* (2013.01); *G01N 33/48721* (2013.01); *G01N 2035/00881* (2013.01)

(58) Field of Classification Search
CPC .......... B01L 2200/10; B01L 2300/023; B01L 2300/024; B01L 2300/027; B01L 2300/0636; G01N 33/4875; G01N 33/48792; G01N 33/48721; G01N 2035/00881
See application file for complete search history.

(56) References Cited

U.S. PATENT DOCUMENTS

| | | | |
|---|---|---|---|
| 5,750,341 | A | 5/1998 | Macevicz |
| 6,210,891 | B1 | 4/2001 | Nyren et al. |
| 6,258,568 | B1 | 7/2001 | Nyren |
| 6,274,320 | B1 | 8/2001 | Rothberg et al. |
| 6,413,792 | B1 | 7/2002 | Sauer et al. |
| 6,627,067 | B1 | 9/2003 | Branton et al. |
| 6,911,132 | B2 | 6/2005 | Pamula et al. |
| 7,001,792 | B2 | 2/2006 | Sauer et al. |
| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,244,559 | B2 | 7/2007 | Rothberg et al. |
| 7,315,019 | B2 | 1/2008 | Turner et al. |
| 7,329,492 | B2 | 2/2008 | Hardin et al. |
| 7,329,860 | B2 | 2/2008 | Feng et al. |
| 7,405,281 | B2 | 7/2008 | Xu et al. |
| 7,595,883 | B1 | 9/2009 | El Gamal et al. |
| 7,815,871 | B2 | 10/2010 | Pamula et al. |
| 7,998,436 | B2 | 8/2011 | Polluck et al. |
| 8,315,817 | B2 | 11/2012 | Kain et al. |
| 9,651,519 | B2 | 5/2017 | Brown et al. |
| 2002/0055100 | A1 | 5/2002 | Kawashima et al. |
| 2002/0189946 | A1 | 12/2002 | Wainright et al. |
| 2004/0002090 | A1 | 1/2004 | Mayer et al. |
| 2004/0096853 | A1 | 5/2004 | Mayer |
| 2004/0241045 | A1* | 12/2004 | Sohl, III ............... E02D 1/02 422/67 |
| 2005/0043894 | A1* | 2/2005 | Fernandez ............. A61B 5/686 128/920 |
| 2005/0064460 | A1 | 3/2005 | Holliger et al. |
| 2005/0130173 | A1 | 6/2005 | Leamon et al. |
| 2005/0191698 | A1 | 9/2005 | Chee et al. |
| 2007/0099208 | A1 | 5/2007 | Drmanac et al. |
| 2007/0128624 | A1 | 6/2007 | Gormley et al. |
| 2008/0009420 | A1 | 1/2008 | Schroth et al. |
| 2008/0108082 | A1 | 5/2008 | Rank et al. |
| 2008/0182757 | A1 | 7/2008 | Heiner et al. |
| 2009/0026082 | A1 | 1/2009 | Rothberg et al. |
| 2009/0100030 | A1 | 4/2009 | Isakson |
| 2009/0127589 | A1 | 5/2009 | Rothberg et al. |
| 2009/0150084 | A1 | 6/2009 | Colwell et al. |
| 2010/0009871 | A1 | 1/2010 | Reed et al. |
| 2010/0048410 | A1 | 2/2010 | Shenderov et al. |
| 2010/0111768 | A1 | 5/2010 | Banerjee et al. |
| 2010/0137143 | A1 | 6/2010 | Rothberg et al. |
| 2010/0187115 | A1 | 7/2010 | Posner et al. |
| 2010/0224494 | A1 | 9/2010 | Chambers et al. |
| 2010/0294663 | A1 | 11/2010 | Weber |
| 2011/0072914 | A1 | 3/2011 | Lebl et al. |
| 2012/0020537 | A1 | 1/2012 | Garcia et al. |
| 2012/0270305 | A1 | 10/2012 | Reed et al. |
| 2012/0322679 | A1 | 12/2012 | Brown et al. |
| 2013/0217106 | A1 | 8/2013 | Jones |
| 2013/0331992 | A1 | 12/2013 | Subramaniam et al. |

FOREIGN PATENT DOCUMENTS

| | | |
|---|---|---|
| WO | WO 2004/018497 | 3/2004 |
| WO | WO 2005/010145 | 2/2005 |
| WO | WO 2007/123744 | 11/2007 |
| WO | WO 2010/034018 | 3/2010 |
| WO | WO 2010/077859 | 7/2010 |
| WO | WO 2011/067559 | 6/2011 |

OTHER PUBLICATIONS

Bentley et al., "Accurate whole human genome sequencing using reversible terminator chemistry", Nature 456:53-59 (2008).
Cockroft, et al., "A Single-Molecule Nanopore Device Detects DNA Polymerase Activity With Single-Nucleotide Resolution", *J. Am. Chem. Soc.* 130(3), 818-820 (2008).
Deamer & Akeson, "Nanopores and nucleic acids: prospects for ultrarapid sequencing," *Trends Biotechnol.* 18, 147-151 (2000).
Dressman et al., "Transforming single DNA molecules into fluorescent magnetic particles for detection and enumeration of genetic variations," *Proc. Natl. Acad. Sci. USA* 100(15) 8817-8822 (2003).
Drmanac et al., "Accurate squencing by hybridization for DNA diagnostics and individual genomics", *Nature Biotechnology* 16, 54-58 (1998).
Fodor et al., "Light-Directed, Spatially Addressable Parallel Chemical Synthesis", *Science* 251(4995), 767-773 (1991).
Healy, "Nanopore-based single-molecule DNA analysis", *Nanomed.* 2(4), 459-481 (2007).
Korlach et al., "Selective aluminum passivation for targeted immobilization of single DNA polymerase molecules in zero-mode waveguide nanostructures", *Proc. Natl. Acad. Sci.* 105(4), 1176-1181(2008).
Levene et al., "Zero-Mode Waveguides for Single-Molecule Analysis at High Concentrations," *Science* vol. 299, 682-686 (2003).
Lizardi et al., "Mutation detection and single-molecule counting using isothermal rolling-circle amplification," *Nat. Genet.* 19:225-232 (1998).
Lundquist et al., "Parallel confocal detection of single molecules in real time", *Opt. Lett.* 33, 1026-1028 (2008).
Ronaghi, et al., "Real-Time DNA Sequencing Using Detection of Pyrophosphate Release", *Analytical Biochemistry* 242(1), 84-9 (1996).
Ronaghi et al., "A Sequencing Method Based on Real-Time Pyrophosphate", *Science* 281(5375), 363-365 (1998).
Ronaghi, "Pyrosequencing Sheds Light on DNA Sequencing", *Genome Res.* 11(1), 3-11 (2001).
Shendure et al., "Accurate Multiplex Polony Sequencing of an Evolved Bacterial Genome," *Science* 309:1728-1732 (2005).
Soni & Meller, "Progress toward Ultrafast DNA Sequencing Using Solid-State Nanopores", *Clin. Chem.* 53:11, 1996-2001 (2007).

* cited by examiner

PORTABLE GENETIC DETECTION AND ANALYSIS SYSTEM AND METHOD

CROSS-REFERENCE TO RELATED APPLICATIONS

The present application is a continuation of U.S. patent application Ser. No. 15/209,351, filed Jul. 13, 2016, which is a continuation of U.S. patent application Ser. No. 13/790,623, filed Mar. 8, 2013, which claims priority from and the benefit of U.S. Provisional Application No. 61/622,773, entitled "PORTABLE GENETIC DETECTION AND ANALYSIS SYSTEM AND METHOD," filed Apr. 11, 2012. Each of the foregoing is hereby incorporated by reference in its entirety.

BACKGROUND

The present disclosure relates generally to a field of genetic analysis, such as for diagnostic sequencing and other purposes. More specifically, the disclosure relates to a portable analysis system that may be carried or transported to desired locations to facilitate sample collection, sample analysis, and further processing.

Genetic sequencing has become an increasingly important area of genetic research, promising future uses in diagnostic and other applications. In general, genetic sequencing involves determining the order of nucleotides for a nucleic acid such as a fragment of RNA or DNA. Relatively short sequences are typically analyzed, and the resulting sequence information may be used in various bioinformatics methods to logically fit fragments together to reliably determine the sequence of much more extensive lengths of genetic material from which the fragments were derived. Automated, computer-based examinations of characteristic fragments have been developed and have been used more recently in genome mapping, identification of genes and their function, and so forth. However, existing techniques are highly time-intensive, and resulting genomic information is accordingly extremely costly to obtain.

A number of alternative sequencing techniques are presently under investigation and development. In such techniques, typically single nucleotides or strands of nucleotides (oligonucleotides) are introduced and permitted or encouraged to bind to the template of genetic material to be sequenced. Sequence information may then be gathered by imaging the sites. In certain current techniques, for example, each nucleotide type is tagged with a fluorescent tag or dye that permits analysis of the nucleotide attached at a particular site to be determined by analysis of image data. Although such techniques show promise for significantly improving throughput and reducing the cost of sequencing, further progress in speed, reliability, and efficiency of data handling is needed.

For example, in certain sequencing approaches that use image data to evaluate individual sites, large volumes of image data may be produced during sequential cycles of sequencing. In systems relying upon sequencing by synthesis (SBS), for example, dozens of cycles may be employed for sequentially attaching nucleotides to individual sites. Images formed at each step result in a vast quantity of digital data representative of pixels in high-resolution images. These images are analyzed to determine what nucleotides have been added to each site at each cycle of the process. Other images may be employed to verify de-blocking and similar steps in the operations.

Genetic analyses of the types described above are presently performed in stationary, and even quite specialized equipment in laboratory, medical facility, research and similar environments. There is a growing need, however, for more flexible systems that can be taken to the field for performing at least some sample collection and analysis. The art has yet to respond to these needs, owing in part to the designs of sample preparation equipment, imaging components, processing needs, and so forth.

BRIEF DESCRIPTION

The present disclosure provides novel approaches to genetic analysis designed to respond to such needs. The techniques are based upon the design of a portable system, such as a hand-held device, that may receive samples, perform nucleic acid detection, such as reading of particular genes or genetic sequences, and at least partial processing of the resulting data. In certain embodiments described, the data may be only partially processed on-board, and data may be transferred to other systems for further processing. Various topologies for the device are envisaged, including fully equipped devices that are able to perform substantial processing, devices that are tethered or communicate wirelessly with other local portable devices, and devices that can do little or no processing, but transfer data to more processing-capable systems for processing. Various usage scenarios are also envisaged that go hand-in-hand with the portable nature of the device. These may greatly simplify the data collection and processing services carried out on the device, limit the degree of analysis necessary depending on the application, and so forth.

In accordance with a first aspect of the disclosure, portable genetic detector may comprise a reading component configured to detect nucleic acids of interest in a biological sample introduced into the detector. A control system is configured to control operation of the reading component. A communications component configured to transmit data produced by the reading component to a remote computer system for analysis.

According to other aspects, portable genetic detector comprises a reading component configured to detect nucleic acids of interest in a biological sample, and a control system configured to control operation of the reading component. A locating component is configured to locate the portable detector as it is displaced to sample locations.

In accordance with further aspects, a portable genetic detector comprises a reading component configured to detect nucleic acids of interest in a biological sample, and a control system configured to control operation of the reading component. A memory circuit is configured to store signature data for target genetic sequence. The processing system is configured to compare data derived from the reading component to the signature data.

The invention offers a number of other variants and innovations, both in terms of a portable detector device, systems in which the detector may be utilized, and method for performing detection and analysis utilizing the advantages and unique benefits of the portable detector.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
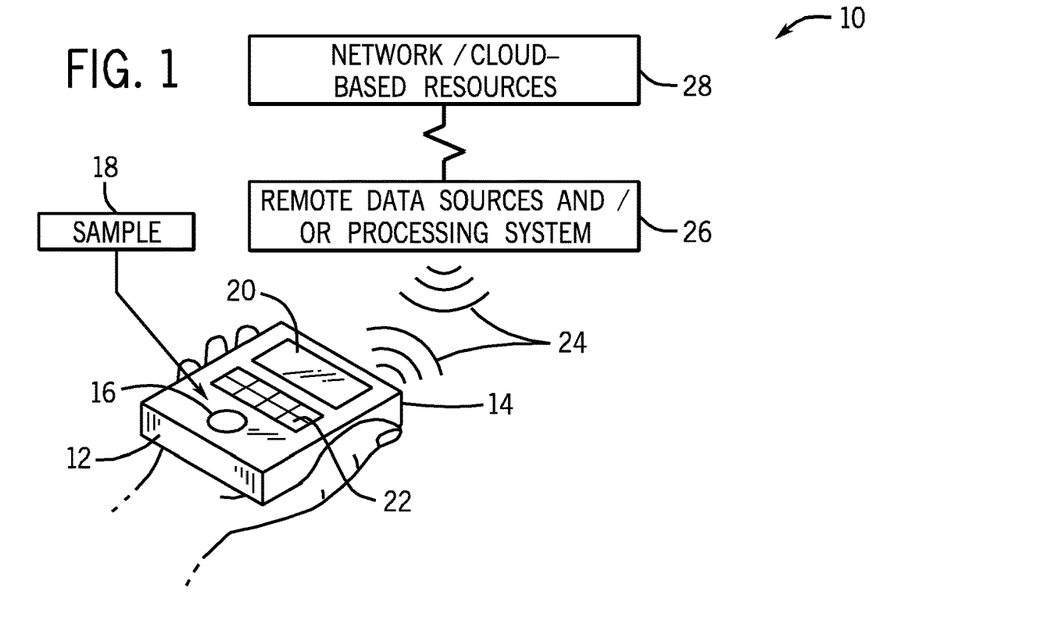
FIG. 1 is a diagrammatical overview of a portable genetic analysis system in accordance with certain aspects of the present techniques.

FIG. 1 illustrates a portable analysis system 10 that is designed to provide ready and easy mobility between locations where samples may be taken and at least partially processed. The system, at its core, comprises a portable detector 12 that is packaged in a housing 14 that have a form factor sized to be hand-held, carried by a user, and used without the assistance of any special transport equipment. That is, the detector itself is sufficiently light to be easily carried and the housing may be configured in any suitable manner to be comfortable and attractive for use. It is contemplated that many different applications and uses may be envisaged for the detector that are opened by virtue of its size and portability. For example, the detector may be used in field applications, such as for environmental pollutant analysis, animal and/or plant and/or microbe detection and population mapping, conflict zone, triage, disaster response, and similar applications, animal and livestock management, to mention only a few. The detector may also find use in medical environments, such as hospitals and clinics.

The portable analysis systems set forth herein are particularly well suited for nucleic acid detection and analysis. As such various embodiments of the system, its components and its uses will be illustrated in the context of nucleic acid detection procedures such as nucleic acid sequencing procedures. It will however be understood that the portable analysis systems can be used to detect other analytes including, but not limited to proteins, small molecules, cells, viruses and other biologically active molecules and particles. In some cases, non-nucleic acid analytes can be detected based on detection of a nucleic acid tag that is generated from an assay using those analytes or that is selected in such an assay. Indeed a portable analysis system of the present disclosure can be used for any of a variety of multi-step chemical detection procedures that involve multiple cycles of chemical processing before a conclusion is reached. The detector can transmit data to remote processing system to store information in time and then process the entire set before a conclusion is reached. In the illustrated embodiment, the detector 12 is designed to receive and prepare samples for analysis. A sample introduction port 16 is thus provided through which a sample 18 may be introduced. The sample itself may consist of genetic material, biological fluids such as blood, biological tissues or cells, crushed or partially prepared samples, environmental samples such as water or other fluid-borne samples, and so forth. As described below, in certain contexts, the sample preparation may be off-loaded from the basic device, although the device could be designed to both prepare samples for analytical detection and perform the analytical detection, or more generally, sample preparation, and detection on-board.

In the illustrated embodiment, the portable detector 12 includes a display 20 on which instructions, feedback, operator selections and options, and so forth may be displayed. An operator interface 22 is provided through which the operator may make selections and input instructions. In certain embodiments, however, these functions could be united, such as in a touch display. Those skilled in the art will also recognize that various functions of the device could be controlled by other interface components, such as buttons, slides, voice recognition systems and the like. The portable detector is designed to communicate with other devices for various purposes. For example, the detector may receive programming and instructions from various data sources as indicated by reference numeral 26. These could be data sources remote or local to the device, at least in a part of the device's life and use. That is, the portable detector may be programmed by a wired or wireless connection to a programming station, charging station or the like when in the vicinity of such equipment. Alternatively, certain of the data needed for operation of the portable detector may be received remotely, such as by wireless networks, based upon any suitable technology and protocol. Moreover, the device is designed to communicate data to one or more remote processing systems, also represented by numeral 26 in FIG. 1.

As described more fully below, the detector will typically perform at least very basic analysis on-board, and may communicate certain results of the analysis to more capable processing systems for further processing. This is particularly the case where the detector will be limited in its own processing capabilities either by the particular processing circuitry utilized, the amount of memory provided, the sophistication of the analyses required, and so forth. Off-loading certain of these capabilities, in certain presently contemplated embodiments, will render the device even more portable and light-weight, while not surrendering capabilities of the overall system that would then include the off-board processing capabilities. Finally, in the illustration of FIG. 1, the remote data resource and processing system may be coupled to network or cloud-based resources. It should be noted, however, that the detector 12 could also be coupled to such resources directly. In general, such resources may provide some or all of the more demanding processing requirements, may be used as a resource for obtaining desired programming, bio-signatures (as discussed below), and so forth.

Where used with cloud-based resources, the portable detector may be considered part of a cloud computing environment for biological data. As used herein, the term "cloud" or "cloud computing environment" may refer to various evolving arrangements, infrastructure, networks, and the like that will typically be based upon the Internet. The term may refer to any type of cloud, including client clouds, application clouds, platform clouds, infrastructure clouds, server clouds, and so forth. As will be appreciated by those skilled in the art, such arrangements will generally allow for use by owners or users of sequencing or detection devices, provide software as a service (SaaS), provide various aspects of computing platforms as a service (PaaS), provide various network infrastructures as a service (IaaS) and so forth. Moreover, included in this term should be various types and business arrangements for these products and services, including public clouds, community clouds, hybrid clouds, and private clouds. Any or all of these may be serviced by third party entities. However, in certain embodiments, private clouds or hybrid clouds may allow for sharing of sequence data and services among authorized users.

Such cloud computing environments may include a plurality of distributed nodes. The computing resources of the nodes may be pooled to serve multiple consumers, with different physical and virtual resources dynamically assigned and reassigned according to consumer demand. Examples of resources include storage, processing, memory, network bandwidth, and virtual machines. The nodes may communicate with one another to distribute resources, and such communication and management of distribution of resources may be controlled by a cloud management module, residing one or more nodes. The nodes may communicate via any suitable arrangement and protocol. Further, the nodes may include servers associated with one or more providers. For example, certain programs or software platforms may be accessed via a set of nodes provided by the owner of the programs while other nodes are provided by data storage companies. Certain nodes may also be overflow nodes that are used during higher load times.

Figure 2:
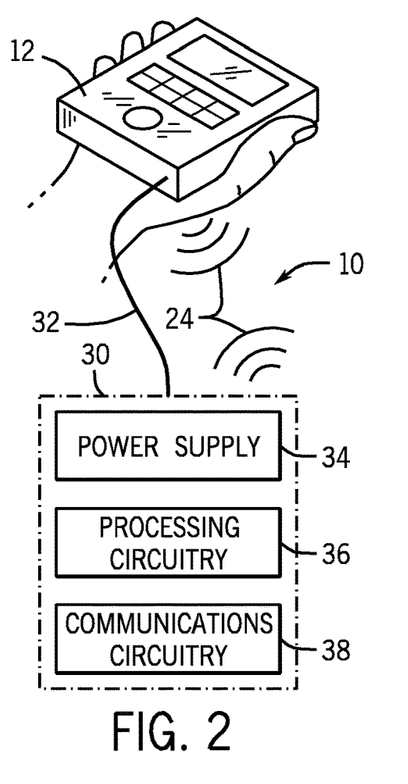
FIG. 2 is a diagrammatical view of a variant of the topology shown in FIG. 1 designed to communicate with a portable support unit.

Several alternative topologies are presently envisaged for the portable detector. In particular, FIG. 2 illustrates a detector 12 that is coupled to a support pack or processing unit 30. The detector 12, in this case, may be thought of as an analytic detection or data acquisition unit, while the support pack may be thought of as a data analysis or processing unit. The support pack may provide various resources that allow the portable detector to be reduced in size and weight, while providing the desired functionality. For example, the support pack could be tethered to the portable detector as indicated generally by reference numeral 32. In addition, or alternatively, these could communicate with one another wirelessly as indicated by reference numeral 24.

In the illustrated embodiment, the support pack 30 comprises a power supply 34, processing circuitry 36 and communications circuitry 38. In this embodiment, at least some of the power for operation of the portable detector 12 can be provided by the power supply 34. The power supply also affords power for operation of the support pack. Alternatively or additionally, the portable detector 12 can include an on-board power supply. The processing circuitry 36 may supplement processing circuitry contained in the portable detector, or in some cases all or virtually all of the processing required by the detector may be provided by the processing circuitry 36 of the support pack. Finally, communications circuitry 36 may be off-loaded from the portable detector and provided in the support pack. Such communications circuitry will allow the system to communicate with local or remote devices, either wirelessly or when physically connected (via a wired connection), as discussed in greater detail below. It should be noted, however, that the support pack need not provide all of these services for the portable detector, and those skilled in the art may recognize other components or services that may be off-loaded from the portable detector to the support pack. In a presently contemplated usage, the portable detector may be hand-held, and the support pack could be carried, such as either on the belt or back of the user.

Figure 3:
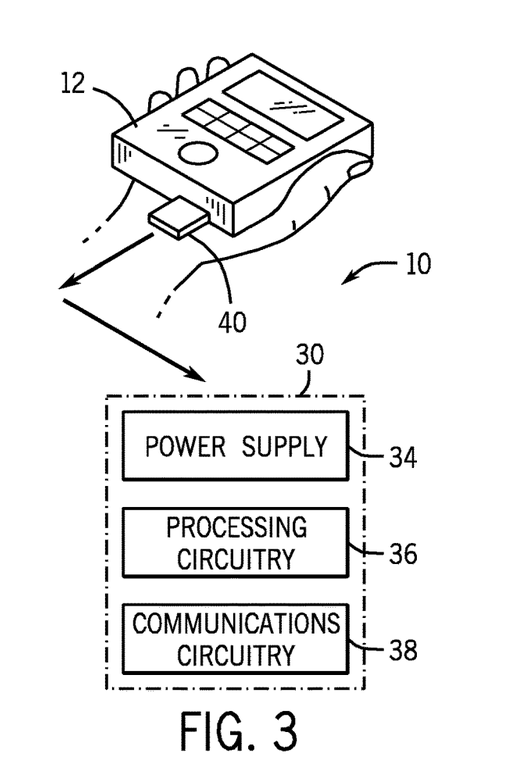
FIG. 3 is a diagrammatical representation of further topology in which a memory support may be used in conjunction with the portable device.

FIG. 3 illustrates a further topology in which the portable detector 12 receives one or more memory devices 40 for storage and communication of raw, partially processed or fully processed and analyzed data. Any convenient memory device may be utilized, such as conventional memory chips, USB flash memories, and so forth. In a field application, the memory device may be utilized with the portable detector to capture certain data, and a user may insert further memory devices when the memory device is full, or to distinguish between different samples, collection points, and so forth. In the embodiment illustrated in FIG. 3, then, the memory device may be inserted into a support pack 30 of the type described with reference to FIG. 2. Alternatively, such memory devices may simply be transported back to a base location where the data may be re-accessed for processing.

Figure 4:
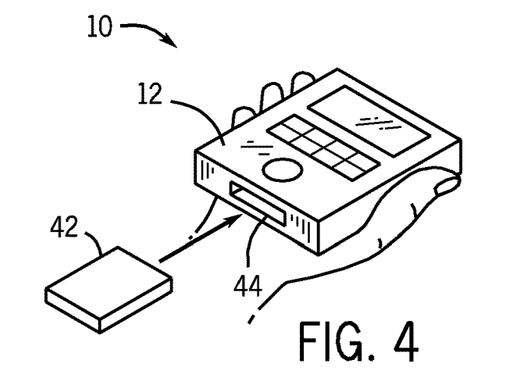
FIG. 4 illustrates a further topology in which the portable device receives a cartridge, such as for sample preparation or management.

FIG. 4 illustrates a further topology in which a removable sample preparation/reading cassette 42 is insertable into the portable detector. The portable detector may contain control and processing circuitry that is designed to interface with the cassette 42. A port 44 is provided in the detector to receive the cassette which is then automatically interfaced with any electrical or electronic traces, pins, pads, and so forth for operation of the detector based upon a sample stored in the cassette. In certain presently contemplated embodiments, for example, the cassette may include both a sample support and certain reagent flow control devices. The cassette may also include reagents for use in nucleic acid detection or sequencing procedures. Still further, where desired, one or more imaging heads or components may be provided in the cassette to allow for the detection of individual nucleotides on a support.

A portable detector can be configured for use with several different types of sample preparation/reading cassettes. For example, different cassettes can be configured to detect different types of analytes. In particular embodiments, one type of cassette can be configured to genomic DNA, a second type of cassette can be configured to detect mRNA and a third type of cassette can be configured to detect proteins. Alternatively or additionally, a sample preparation/reading cassette can include machine readable code(s) (or other indicia), such as one or more RFID tags, barcodes or the like, that direct the portable detector to run a particular process or protocol on the cassette. Taking for example a cassette that is configured to detect genomic DNA, one or more codes can direct the portable detector and, in turn the analysis system, to run a whole genome sequencing or exome sequencing protocol, for example, to identify allelic variants at particular genetic loci. As another example, a cassette that is configured for detection of mRNA can include code(s) that instruct the portable detector and related analysis system to determine expression levels for one or more RNA species, for example, in a digital gene expression analysis. In the example of a cassette that is configured for protein detection, code(s) can instruct the portable detector to determine the presence or absence of one or more proteins of interest, for example, based on detection of nucleic acid tags obtained from a protein binding assay.

Figure 5:
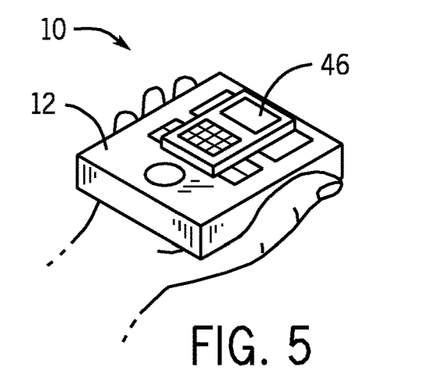
FIG. 5 is still a further topology in which the portable analysis system receives a removable interface, such as a smartphone.

Finally, FIG. 5 illustrates further topology in which the portable detector 12 is capable of receiving a removable interface/processing device 46. It is contemplated that such devices may be specially designed for use with the portable detector, although commercially available devices may be adapted for this purpose. Thus, the device 46 could comprise a smartphone, personal digital assistant, or any suitable device capable of offering an interface in providing at least some processing and/or control capabilities.

Figure 6:
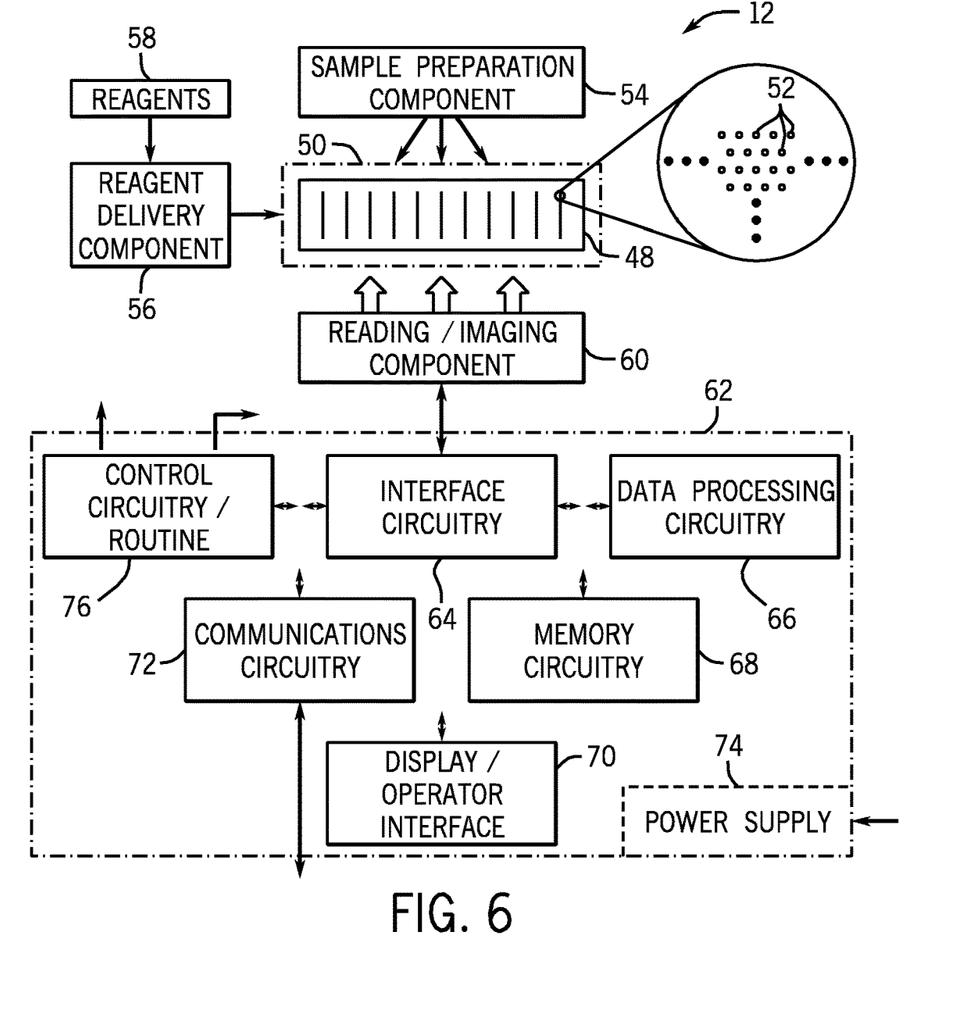
FIG. 6 is a diagrammatical representation of certain of the functional components that may be included in the portable analysis system.

FIG. 6 illustrates certain of the physical and functional components of an exemplary portable detector 12. The detector is designed to operate on a support 48 that holds samples of genetic material, such as material collected by displacement of the portable detector to one or more collection locations. The support 48 may be contained in a flow cell 50 that allows for reagents, flushing fluids, deblocking chemistry, and so forth to be moved over the support to facilitate imaging and analysis. The support 48, in the illustrated embodiment, comprises a plurality of sites 52 disposed as an array on a surface of the support. Each site in the array may, once the sample is prepared for reading, comprise a single nucleic acid molecule or a population comprising several copies of a nucleic acid molecule (i.e. several species having the same nucleic acid sequence). The sample preparation may consist of cleaving or separating genetic material and disposing the genetic material at such sites. The sample preparation can further include amplification of the genetic material before or after the genetic material is disposed at the sites. Examples of supports, flow cells, and technologies for sample preparation are described, for example, in US 2010/0111768 A1 and U.S. Ser. No. 13/273,666, which are hereby incorporated by reference.

For ease of explanation, the systems, devices, and methods of the present disclosure are exemplified herein with regard to optically-based SBS procedures. For example, flow cell supports useful for optical detection of nucleic acid colonies in SBS procedures are set forth above. In SBS, extension of a nucleic acid primer along a nucleic acid template is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. A plurality of different templates can be subjected to an SBS technique on a surface under conditions where events occurring for different templates can be distinguished. For example, the templates can be present on the surface of an array such that the different templates are spatially distinguishable from each other. Typically the templates occur at features each having multiple copies of the same template (sometimes called "clusters" or "colonies"). However, it is also possible to perform SBS on arrays where each feature has a single template molecule present, such that single template molecules are resolvable one from the other (sometimes called "single molecule arrays").

Flow cells provide a convenient substrate for housing an array of nucleic acids. Flow cells are convenient for sequencing techniques because the techniques typically involve repeated delivery of reagents in cycles. For example, to initiate a first SBS cycle, one or more labeled nucleotides, DNA polymerase, etc., can be flowed into/through a flow cell that houses an array of nucleic acid templates. Those features where primer extension causes a labeled nucleotide to be incorporated can be detected, for example, using methods or apparatus set forth herein. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use in a portable detector of the present disclosure are described, for example, in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

It should be noted that other types of supports and genetic material reading technologies besides the SBS procedures exemplified above may be utilized in a portable detector or portable genetic analysis system. Other sequencing procedures that use cyclic reactions can be used, such as those wherein each cycle can include steps of delivering one or more reagents to nucleic acids. A particularly useful sequencing procedure is pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to a portable detector of the present disclosure are described, for example, in WIPO Pat. App. Ser. No. PCT/US11/57111, US 2005/0191698, U.S. Pat. Nos. 7,595,883, and 7,244,559, each of which is incorporated herein by reference.

Sequencing-by-ligation reactions are also useful including, for example, those described in Shendure et al. *Science* 309:1728-1732 (2005); U.S. Pat. Nos. 5,599,675; and 5,750,341, each of which is incorporated herein by reference in its entirety. Some embodiments can include sequencing-by-hybridization procedures as described, for example, in Bains et al., *Journal of Theoretical Biology* 135(3), 303-7 (1988); Drmanac et al., *Nature Biotechnology* 16, 54-58 (1998); Fodor et al., *Science* 251(4995), 767-773 (1995); and WO 1989/10977, each of which is incorporated herein by reference. In both Sequencing-by-ligation and sequencing-by-hybridization procedures, target nucleic acids can be immobilized on a solid support and cycles of oligonucleotide delivery and detection can be repeated. Fluidic systems for SBS methods as set forth herein or in references cited herein can be readily adapted for delivery of reagents for sequencing-by-ligation or sequencing-by-hybridization procedures.

Typically, the oligonucleotides are fluorescently labeled and can be detected using fluorescence detectors similar to those described with regard to SBS procedures herein or in references cited herein.

Some embodiments can utilize nanopore sequencing. In such embodiments, target nucleic acid strands, or nucleotides exonucleolytically removed from target nucleic acids, pass through a nanopore. The nanopore can be a synthetic pore or biological membrane protein, such as α-hemolysin (Deamer & Akeson *Trends Biotechnol.* 18, 147-151 (2000), incorporated herein by reference), *Mycobacterium smegmatis* porin A (MspA, WO 2010/034018 A2, incorporated herein by reference) or solid-state pores (U.S. Pat. Nos. 6,627,067 or 6,413,792, each of which is incorporated herein by reference). As the target nucleic acids or nucleotides pass through the nanopore, each type of base can be identified by measuring fluctuations in the electrical conductance of the pore (U.S. Pat. No. 7,001,792; Soni & Meller, *Clin. Chem.* 53, 1996-2001 (2007); Healy, *Nanomed.* 2, 459-481 (2007); and Cockroft, et al. *J. Am. Chem. Soc.* 130, 818-820 (2008), the disclosures of which are incorporated herein by reference in their entireties). Thus, a device of the present disclosure can include a detector of electrical properties of nucleic acids, nucleotides and/or their environment.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides, or with zeromode waveguides. The illumination can be restricted to a zeptoliter-scale volume around a surface-tethered polymerase such that incorporation of fluorescently labeled nucleotides can be observed with low background (Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference in their entireties).

Some SBS embodiments include detection of a proton released upon incorporation of a nucleotide into an extension product. For example, sequencing based on detection of released protons can use an electrical detector and associated techniques that are commercially available from Ion Torrent (Guilford, C T, a Life Technologies subsidiary) or sequencing methods and systems described in US 2009/0026082 A1; US 2009/0127589 A1; US 2010/0137143 A1; or US 2010/0282617 A1, each of which is incorporated herein by reference in its entirety.

Where desired, a portable detector may comprise a sample preparation component 54 that is configured, for example, to fragment, separate, distribute and/or amplify nucleic acid samples for detection in a sequencing procedure such as one or more of those set forth above. Nucleic acid samples can be fragmented, for example, using sonication, passage through a nozzle that forms tiny droplets (nebulisation), chemical cleavage, enzymatic cleavage, heat and/or radiation. The fragmented nucleic acids can optionally be purified or size selected prior to other sample preparation steps or prior to detection steps. Useful procedures for size selection include, but are not limited to, isotachophoresis (see, for example, US 2002/0189946 A1, US 2010/0224494 A1, and US 2010/0294663 A1, each of which is incorporated herein by reference) or droplet micro-actuation by electrowetting (see, for example, U.S. Pat. Nos. 7,998,436, 7,815,871, 6,911,132, and US 2010/0048410 A1, each of which is incorporated herein by reference). Hardware and/or processes described in the aforementioned references can be used in a portable detector of the present disclosure.

In some embodiments, sample preparation can include steps of attaching nucleic acids to a surface and amplifying the nucleic acids on the surface prior to or during sequencing. For example, amplification can be carried out using bridge amplification to form nucleic acid clusters on a surface. Useful bridge amplification methods are described, for example, in U.S. Pat. No. 5,641,658; US 2002/0055100 A1; U.S. Pat. No. 7,115,400; US 2004/0096853 A1; US 2004/0002090 A1; US 2007/0128624 A1; or US 2008/0009420 A1, each of which is incorporated herein by reference. Another useful method for amplifying nucleic acids before or after attachment to a surface is rolling circle amplification (RCA), for example, as described in Lizardi et al., *Nat. Genet.* 19:225-232 (1998) and US 2007/0099208 A1, each of which is incorporated herein by reference. Emulsion PCR on beads can also be used, for example as described in Dressman et al., *Proc. Natl. Acad. Sci. USA* 100:8817-8822 (2003), WO 05/010145, US 2005/0130173 A1 or US 2005/0064460, each of which is incorporated herein by reference.

Various combinations of the above sample preparation process steps can occur in a portable detector of the present disclosure. Particularly useful arrangements for integrating sample preparation with nucleic acid sequencing detection apparatus are provided in WO 2010/077859 A2, and U.S. Ser. No. 61/556,427, each of which is incorporated herein by reference. It will be understood, that some or all of the sample preparation process steps exemplified herein or in the references cited herein can occur in a portable detector of the present disclosure. Some steps however, can be carried out prior to loading a sample (or sample-bearing substrate) into a portable detector. For example, nucleic acid fragmentation, size purification and amplification can be carried out to obtain amplified nucleic acid fragments and the amplified nucleic acid fragments can then be loaded as the 'sample' into a portable detector.

The device may also support reagent delivery components 56 that allow for the control of flow of chemistry utilized in performing the analysis of the sample. Reagents 58 may also be carried on the device, or these could be provided separately (e.g., in one or more cartridges, capsules, vials, cassettes, and so forth). For example, reagents can be provided to a portable detector of the present disclosure in the form of a cartridge as described in U.S. patent application Ser. No. 13/273,666, which is incorporated herein by reference. The cartridge can contain reservoirs for the reagents absent a flow cell or other fluidic components. Alternatively, the cartridge can include fluidic components such as one or more valves, pressure sources (e.g. pumps), fluidic lines and other components used to actively manipulate the fluids in the cartridge. The cartridge can also include one or more integrated flow cells or other sample detection chambers. Exemplary cartridges having fluidic components and integrated flow cells that can be adapted for use with a portable detector of the present disclosure are described in U.S. Pat. App. Ser. No. 61/619,784, which is incorporated herein by reference. Further examples of reagents and reagent delivery components that can be readily adapted for use in a portable detector, especially for nucleic acid sequencing embodiments, are described, for example, in US 2010-0009871 A1; US 2010-0187115 A1; US 2010-0111768 A1; and US2011-0072914 A1, which are hereby incorporated by reference.

In a presently contemplated embodiment, the detector further comprises reading/imaging components 60. As will be appreciated by those skilled in the art, the chemistry utilized for genotyping, sequencing, and similar genetic processing may be based upon compounds that fluoresce when illuminated by particular wavelengths of light, such as from laser sources. The fluorescent light signals given off by these compounds, once attached to the genetic material at the sites, can be imaged by an optical imaging head or circuitry, such as circuitry including charge coupled devices, filters, and so forth. These imaging systems may be miniaturized to facilitate their use in the portable detector. In certain embodiments, the reading/imaging components may move with respect to the support, or these may be stationary with respect to the support, depending upon such factors as the size of the support, the size of the reading/imaging component (e.g., a read head) the resolution of the imaging components, the density of the sites on the support, and so forth. Examples, of reading/imaging components are described, for example, in US 2010-0111768 A1; U.S. Pat. No. 7,329,860, U.S. patent application Ser. No. 13/273,666 or U.S. Pat. App. Ser. No. 61/619,784, which are hereby incorporated by reference.

The reading/imaging components need not be capable of optical detection for all embodiments of the invention. For example, the reading/imaging component can be an electronic detector used for detection of protons or pyrophosphate (see, for example, US 2009/0026082 A1; US 2009/0127589 A1; US 2010/0137143 A1; or US 2010/0282617 A1, each of which is incorporated herein by reference in its entirety) or as used in detection of nanopores (U.S. Pat. No. 7,001,792; Soni & Meller, *Clin. Chem.* 53, 1996-2001 (2007); Healy, *Nanomed.* 2, 459-481 (2007); and Cockroft, et al. *J. Am. Chem. Soc.* 130, 818-820 (2008), each of which is incorporated herein by reference).

As further illustrated in FIG. 6, the portable detector will have certain on-board circuitry, indicated collectively by reference numeral 62. This circuitry may include, for example, interface circuitry 64 designed to communicate with the reading/imaging component 60 to receive raw signal data (e.g. imaging data) for primary analysis, filtering, compression, and so forth. Data processing circuitry 66 is provided, and may include any suitable type of processor, such as microprocessors, field programmable gate arrays, and so forth. As described more fully below, the processing circuitry 66 may perform initial operations on the raw data received from the reading/imaging component 60, and may stop at the initial primary processing, or may carry on more sophisticated processing designed to recognize particular markers, genes, traits, individuals, and so forth. Memory circuitry 68 supports the processing circuitry 66 and may store programming carried out by the processing circuitry 66. Moreover, the memory circuitry may serve to store raw, processed or any other data received or utilized by the interface circuitry 64 or processing circuitry 66.

A display/operator interface 70 is provided as described above. This may include a visual display and one or more buttons or locations for touching by the user, touch screens, and so forth. The display/operator interface 70 may also allow for certain audible commands, warnings, and so forth to be received and/or output by the device. Communications circuitry 72 allows the detector to communicate with other devices, both local and remote as described above. Such communications circuitry may be based upon any suitable communications technology or protocol, such as Internet protocols, cellular telephone protocols, wireless protocols, wired data communication protocols, and so forth. A power supply 74 is provided to power the various functions of the device, particularly the data processing circuitry, display, communication circuitry, and so forth. The power supply will typically comprise one or more batteries, voltage regulators, amplifiers, and so forth that allow for extended use of the portable detector between battery changes or recharges. An arrow in FIG. 6 indicates that the power supply 74 may be rechargeable. Finally, control circuitry/routines 76 are provided for coordinating the operation of the various components, particularly the reading/imaging component, the processing components, the communication components, the display, and so forth. Instructions and routines for the control circuitry 76 may be stored in the memory circuitry 68. Where provided, the control circuitry 76 may also regulate operation of the reagent delivery component, any sample preparation component, and so forth.

As summarized above, some or all of the circuitry may be off-loaded from the portable detector. The circuitry may be provided in a support pack of the type described above. This is particularly the case for the power supply 74 illustrated in FIG. 6, certain of the processing circuitry 66, the communications circuitry 72, even of certain of the control circuitry 76.

Figure 7:
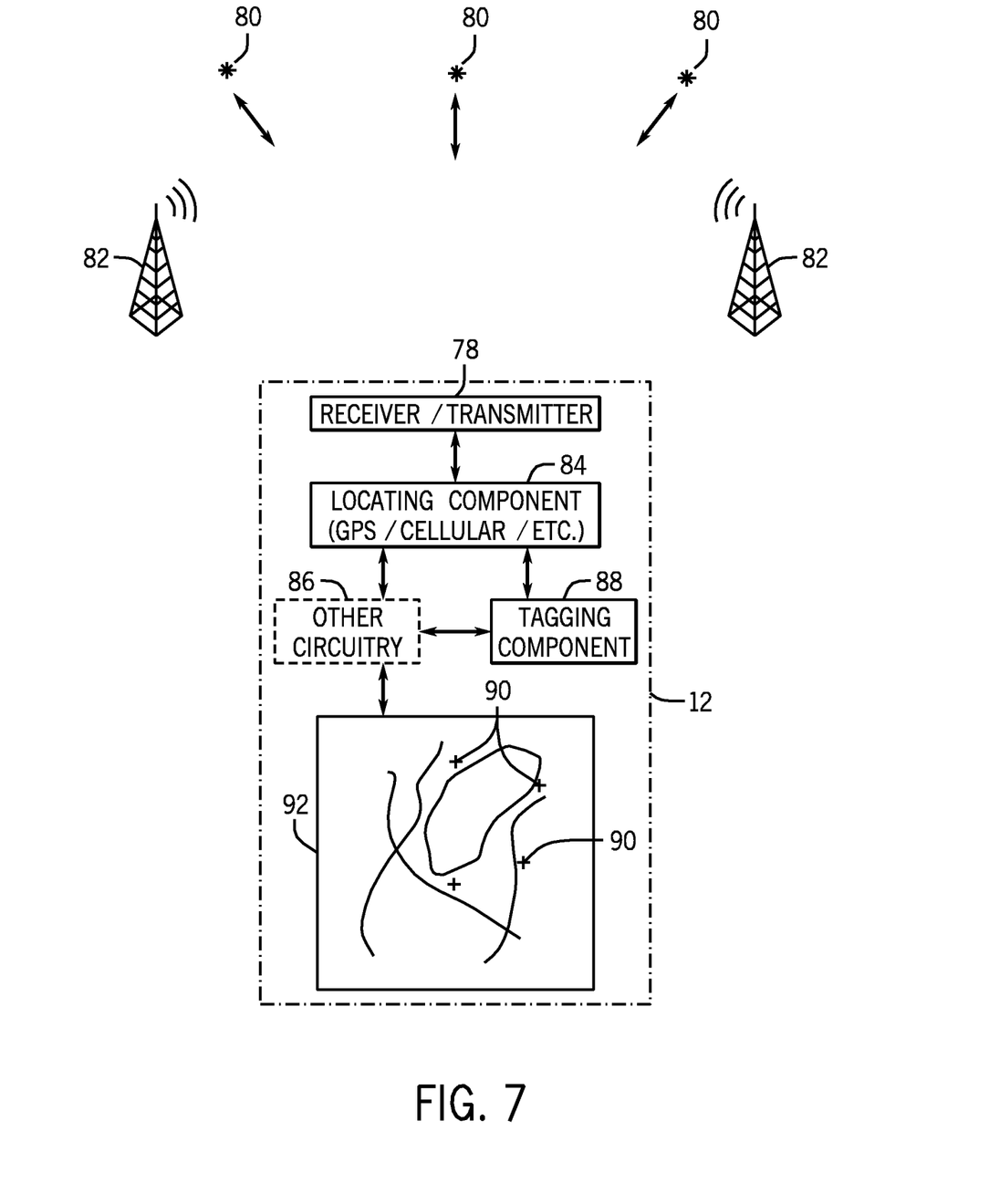
FIG. 7 is a diagrammatical representation of a portable analysis system that incorporates means for locating the system and places where samples are taken for analysis.

FIG. 7 illustrates a further embodiment of the portable detector that includes circuitry for determining the location of the detector, such as for tracking locations where samples are procured or should be procured, or both. In this embodiment, the detector includes a receiver/transmitter 78 as designed to exchange signals with one or more locating device. For example, the receiver/transmitter 78 may comprise a GPS receiver designed to receive signals from geostationary satellites 80 in accordance with existing technologies. Alternatively, the receiver/transmitter 78 may include cellular data exchange circuitry designed to exchange signals with cellular transmitters/receivers 82. Where desired, both of these technologies, as well as others, subsequently developed may be provided in the device. The receiver/transmitter is coupled to a locating component 84 which is capable of triangulating or otherwise computing the location of the device based upon the received signals. The locating component 84 is coupled to the other circuitry 86 as described above, such as for providing control and power to the locating component. A tagging component 88 may be provided which may interface with data processing circuitry to place a location tag on data acquired by the reading/imaging component, or to data processed by the data processing circuitry. Locations 90 of samples may be located on a map 92 that may be displayed on the interface of the detector. As will be appreciated by those skilled in the art, such locations may indicate points where samples should be taken, points where samples have been taken, or both. It is presently contemplated that such functionality may be useful in certain applications, such as for environmental testing, mapping of flora and fauna, persons, animals, livestock, and so forth. As noted, the location information may be stored in a file with any processed data to indicated such factors as the time at which the sample was taken and/or processed, the location at which the sample was taken and/or processed, any other environmental or input information provided by the user via the interface, the identification of the person or persons who took the sample, the identification of the portable detector, and so forth.

Figure 8:
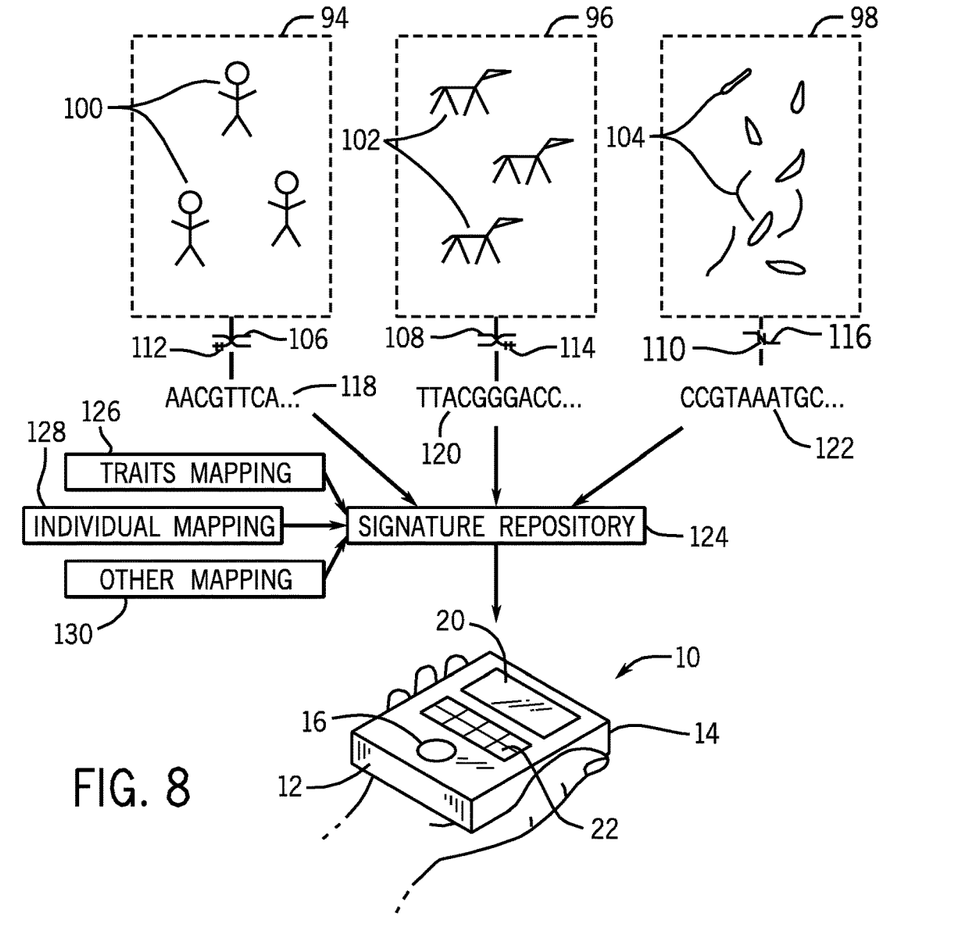
FIG. 8 is a diagrammatical representation of an exemplary use case in which signatures are stored on the portable analysis system for identifying matches in the field.

As noted above, a number of uses may be envisaged for the portable detector. One family of uses presently contemplated involves the identification of people, animals and stocks, plants, microbes, pathogens, and so forth. Moreover, it is presently contemplated that, as described more fully below, the reduction of analysis to a particular candidate trait or traits, and/or to a particular candidate individual or individuals, may greatly facilitate the use of the portable detector, and assist in reduction of the size and complexity of the detector by facilitating processing. FIG. 8 illustrates an exemplary set of scenarios of this type. As shown in FIG. 8, the portable analysis system may be utilized to locate and/or identify sub-populations 94, 96, and/or 98, which correspond to human beings 100, animals or stock 102, and one or more microbes 104. Each of these populations may be associated with genetic material 106, 108, and 110, respectively. Within this genetic material, then, particular sequences or segments of material, each comprising a series of nucleotides, may be identified as indicated by reference numerals 112, 114, and 116, respectively. Each of these segments may then be characterized by the particular nucleotides and their unique order to create signatures identified in FIG. 8 by reference numerals 118, 120, and 122.

It should be noted that in various use cases the segments of interest and the consequent signatures may correspond to such parameters as a population of individuals sharing a common trait or gene, particular individuals separately identifiable by strings of genetic material, particular plants or animals identifiable by such strings, individual microbes similarly identifiable, including strings of such microbes, and so forth. Similarly, the signatures may encode particular traits of interest, such as physical traits desirable or more generally of interest in managed stocks, animal, and plant populations.

The signatures for the sub-population of interest may be stored in a signature repository 124 which may be loaded onto the portable detector or stored separately. In addition to the signatures themselves, the repository may receive various mappings of traits 126, individuals 128 and other mappings 130, such as for species, group identifications, and so forth. These signatures may be utilized, as discussed more fully below, in the analysis performed by the portable detector. An advantage of using a signature repository is that analysis, for example, in a re-sequencing or sequence alignment protocol can occur more rapidly and using fewer computational resources than would be necessary when using standard databases having more comprehensive and larger collections of reference sequences.

By way of example, the portable detector may be used in conflict zones to identify individuals in the field, and in many applications for disaster relief, humanitarian aid, and so forth. In such situations, individuals may become separated from a family, military unit or other group, individuals may be dispersed or individuals may be in need of assistance. Where possible, the portable detector may receive samples for individuals and determine whether a match for a known signature for the individual can be made. A signature repository used for determining such matches can be custom tailored to the query at hand. For example, in a conflict zone application, the signature repository can include only sequences previously acquired for soldiers who were deployed to the particular conflict field or theater of conflict being investigated. Alternatively, a larger data repository can be used, for example, including sequence data for an entire army, but weighting factors can be used during the comparison analysis based on information and belief as to likely candidates in a particular scenario. Similar signature repositories can be made for other subsets of individuals such as members of a particular family, citizens of a particular country, state, city or other region, individuals having a criminal record, individuals suspected of a particular criminal activity or the like. In connection with localization techniques described above, the individuals could be tagged based upon their location, at least at the time of sampling and/or processing. Similarly, in environmental and agricultural applications, particular plant varieties, hybrids, genetically modified plants, and the like may be tracked and located based upon specific signatures for the target population of interest. Traits of managed livestock may also be determined in a similar manner. The system may thus afford selection of individuals for reproduction or separating from groups, and so forth.

Thus, an individual whose genomic material is tested using a portable detector can constitute a candidate for inclusion in a group of individuals who share one or more of the genetic characteristic that are detected by the portable detector. The group against which an individual is compared can be a predefined group such as a military unit suspected or believed to be associated with a candidate human individual, a family suspected or believed to be associated with a candidate human individual, a herd of animals suspected or believed to be associated with a candidate stock animal, a crop variety suspected or believed to be associated with a candidate individual plant or the like.

Figure 9:
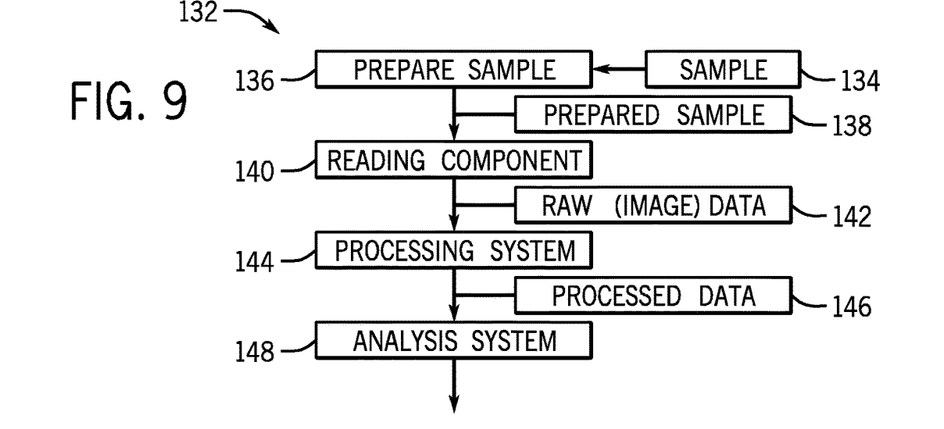
FIG. 9 is a process flow diagram illustrating the various stages of sample and data processing that may be carried out in the portable analysis system.

FIG. 9 is an exemplary diagram illustrating a process flow 132 that may be carried out in the portable detector. In general, the process begins with the sample 134 which is collected, such as from one or more locations, individuals or any other desired source. A sample preparation phase 136 will generally comprise one or more of the steps set forth previously herein, optionally including one or more of isolation of genetic material from the sample, cleaving of the genetic material into smaller segments, and attachment of the smaller segments to the sites on a support, where such support processing is performed. The sample preparation phase may also include amplification and other operations designed to improve the reliability and signal-to-noise ratio in the acquired data.

A resulting prepared sample 138 is then provided to a reading component 140. In several, but not all, presently contemplated embodiments the reading component allows for optical imaging of the genetic material of the sample. The sample may be further processed, particularly when sequencing is desired, to read successive nucleotides in a string of nucleotides at the sites on the sample support for sequencing analysis. The reading component produces raw data 142, which will typically include image data comprising pixilated values for the genetic materials at each of the sites, as well as for spaces between these sites. This raw image data may then be processed by the processing system 144, such as to eliminate un-needed image data (e.g., corresponding spaces between sites) and to determine the type of genetic material (e.g., nucleotides) at the sites. Exemplary methods for masking or compressing image data and that can be used in accordance with the systems, methods and devices herein are described in US 2008/0182757 A1 and US 2012/0020537 A1, each of which is incorporated herein by reference.

The processed data 146 resulting from this primary analysis may then be fed to analysis system 148. This analysis system may determine, based upon the data drawn from the images, whether certain genetic material of interest is present in the sample, whether a match to a target is identified, and so forth. The analysis system may also determine, where such programming is provided, particular sequences of interest, and may assemble sequences into longer sequences for identification of individuals, traits, and so forth. As noted above, where desired, at any stage in this process data may be off-loaded to associated components for processing, or the data may simply be stored and transmitted to other systems for more sophisticated processing. It is presently contemplated that initial embodiment of the portable detector, such off-loading may be very useful in reducing the processing needs, programming requirements, power requirements of the device, and allowing for quick and easy access to a certain level of useful information. As more rapid and capable processing circuits become available, then, these may be utilized in later versions of the detector to enhance the turn-around on processing and analysis, enable more sophisticated processing to take place, and so forth.

Figure 10:
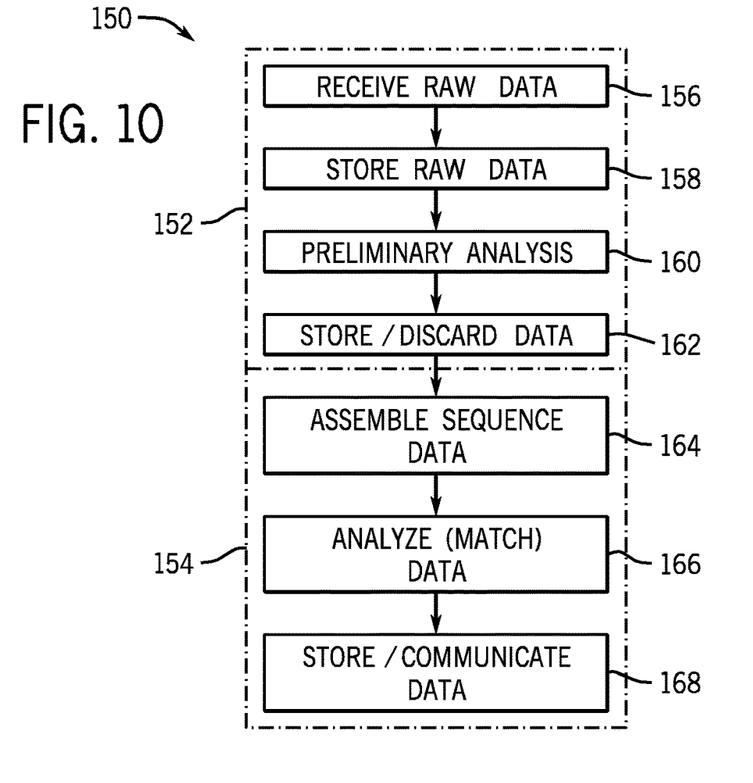
FIG. 10 is a flow chart illustrating exemplary steps in primary and secondary processing of data for analysis.

As described above, the portable detector and analysis system may perform various types of analysis, extending from simple raw image processing to primary analysis, to matching of individual sample donors and populations, to more sophisticated sequencing operations. Certain of the processes are illustrated diagrammatically in FIG. 10. In general, FIG. 10 illustrates data analysis 150 as divided between primary analysis 152 and secondary analysis 154. Again, certain of the primary analysis 152 may be off-loaded from the device, and some or all of the secondary analysis 154 may off-loaded. However, the various phases of analysis are described here to provide an indication of the type of data processing and analysis that may be performed on the device.

In the primary analysis 152, for example, the processing circuitry may receive raw data as indicated at step 156. This raw data may be stored as indicated at 158. However, in presently contemplated embodiments not all of the raw data is permanently or semi-permanently stored following primary analysis as indicated at step 160. As discussed above, this primary analysis may consist of eliminating certain of the image data not corresponding to sites of interest. The primary analysis may also identify particular genetic material (e.g., nucleotides) by virtue of particular wavelengths at which attached material fluoresces under the influence of stimulating light (e.g., from lasers included in the reading component). The result of the primary analysis, as discussed above, may be stored, or some of the data may be discarded as indicated at step 162. The resulting stored data may comprise a data file which identifies one or more nucleotides detected at individual sites on a support along with addresses of these sites.

The secondary analysis 154 may then include assembly of certain sequence data, and/or comparison to a known sequence, and/or counting of particular sequences, etc. where sequencing is performed. As will be appreciated by those skilled in the art, such operations may include the assembly of a list of nucleotides detected at individual sites through successive steps in reagent application to the support, attachment of tags or markers to the genetic materials at the individual sites, and so forth. The resulting data may comprise relatively small lengths of sequences of these nucleotides by individual sites. The processing at step 164 may further include analysis of the resulting small segments to accumulate larger segments or sequences of nucleotides in the sample.

Further, at step 166, these sequences may be compared to certain known genes, traits, signatures for individuals, species, and so forth. Finally, the processing may end with storage and communication of the data as indicated at steps 168. Of course, where a processing is terminated on the portable detector at an earlier stage, such data communication may also occur then. Still further, where raw or semi-processed data is produced by the device, this may be stored on a memory support that is removable from the device for conveyance to another storage and/or analysis system as described above.

Figure 11:
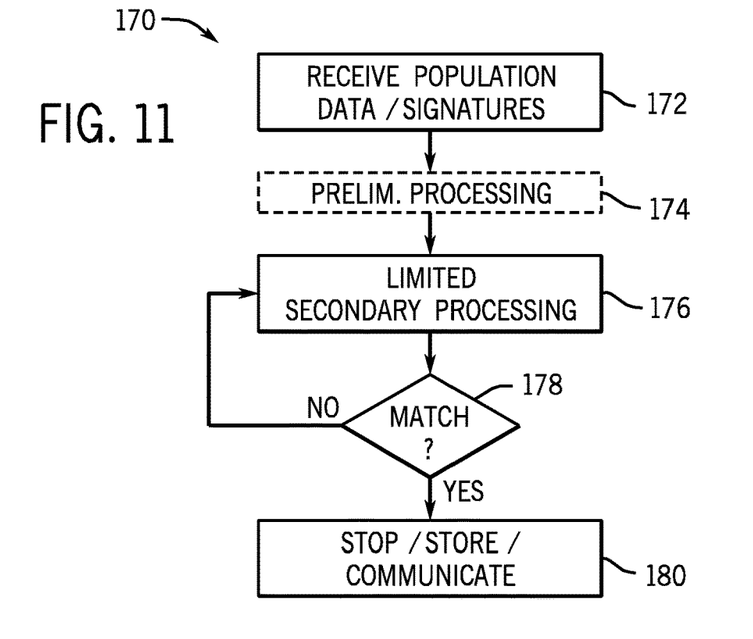
FIG. 11 is a flow chart illustrating a truncated or "process-to-match" technique further facilitating processing within the portable analysis system.

As noted above, certain types of processing may be performed on the portable detector that may greatly assist in affording usable results while reducing the processing demands on the detector itself. The affect of relaxed processing demands may allow for a lighter and faster device capable of providing useful output in a range of applications. FIG. 11 illustrates exemplary processing in a "process-to-match" approach. The processing, designated generally by reference numeral 170, may begin with receiving population data or signatures at step 172. As noted above with reference to FIG. 8, such signatures may correspond to individuals, groups of individuals, animal and plant populations, microbes, or any features or traits of these. Preliminary processing is then carried out as indicated by reference numeral 174 which may be similar to that summarized above with reference to FIG. 10. This preliminary processing may be generally similar to that described above during phase 152 illustrated in FIG. 10. At step 176, then, limited secondary processing may be performed. In the presently contemplated embodiment, this limited secondary processing may consist of assembling of sequences of nucleotides from the information collected from the individual sites on the support. Longer sequences of these nucleotides may then be assembled based upon generally known informatics techniques. At step 178, then, based upon such sequences, the system may determine whether a match to an individual, trait, species, or any sub-population is possible. Because a limited number of signatures may be of interest, this match may be performed relatively quickly as compared to sequencing an entire genome. Once sufficient sequencing and comparison has been made to confirm a positive match, the processing may be stopped and the results stored and, where desired, communicated to external devices, as represented at step 180.

In accordance with the process exemplified in FIG. 11, once a positive match has been confirmed, instructions can be communicated to the portable detector (or to the user of the portable detector) to stop the sequencing procedure. Thus, unnecessary or unwanted consumption of sequencing reagents can be avoided as can unnecessary waste of time. If desired, a new sample can be loaded on the portable detector and sequenced. Furthermore based on the information obtained from a first portable detector, instructions can be communicated to one or more other portable detectors or to the users of the other portable detector(s) to modify schedules or planned procedures. For example, if sufficient information has been obtained from the group of portable detectors the current sequencing procedures can be halted for all of the portable detectors. Alternatively or additionally, one or more of the other portable detectors can be tasked with new instructions regarding samples to evaluate or new priorities can be set with regard to a group of samples that is in the queue for one or more portable detectors, respectively. The group of portable detectors (or their users) that receive such instructions can be determined based on any number of criteria including, but not limited to, proximity to a particular location where candidate individuals or samples are located (for example, as determined from GPS information transmitted from the portable detectors), predefined instructions as to the samples to be evaluated, or optimization of workload spread across a network of portable detectors (or their users).

A decision process similar to that shown in FIG. 11 can be based on balancing costs and benefits. For example, processing may begin with receiving nucleic acid sequencing data from one or more portable detectors. Primary processing can then carried out, followed by secondary processing.

However, during either or both processing steps, the system can be evaluating factors such as costs (in money or time) of data acquisition, data computation, data storage and data transmission. Once costs and benefits are determined to be balanced or to have reached an otherwise desired level, the processing may be stopped and the results stored and, where desired, instructions can be communicated to external devices. For example, at a decision step, based upon the evaluation of such factors, the system may determine whether to proceed with sequencing at one or more of the portable detectors or not. An instruction to halt or pause sequencing can be sent to one or more of the portable detectors in response. Similar evaluation and decision processes can be carried out based on achieving a desired level of data quality or data quantity. For example, data collection and analysis can be allowed to proceed until a desired data quality score is achieved (for example, a Q score of 30) and/or until a desired sequence coverage is achieved (for example, 10×, 20× or 30× sequence coverage for one or more regions of a genome of interest). While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A portable genetic detector system comprising:
   a plurality of portable detectors, wherein each respective portable detector of the plurality of portable detectors comprises:
      a housing;
      an interface disposed on or in the housing and configured to receive input from an operator to control operation of the respective portable detector;
      a sample receiving component configured to receive a biological sample;
      a reader configured to detect nucleic acids of interest in the biological sample to generate sample data;
      a control system programmed to control the operation of the respective portable detector;
      a transceiver configured to output the sample data generated by the reader, wherein the sample data comprises data identifying nucleotides present in the biological sample; and
      a display configured to display information related to the operation of the respective portable detector; and
   a remote processing system in communication with each of the plurality of portable detectors via a wireless connection and separate from the plurality of portable detectors, wherein the remote processing system comprises:
      communications circuitry configured to receive the sample data of the biological sample of each of the plurality of portable detectors, wherein the biological sample of each of the plurality of portable detectors corresponds to a different candidate sample of a plurality of candidate samples; and
      a processor programmed to analyze the sample data of a first candidate sample of the plurality of samples from a first portable detector to generate at least one analysis output comprising sequencing assembly data based on the identified nucleotides of the first portable detector of the plurality of portable detectors and cause the communications circuitry to provide one or more instructions, based on the at least one analysis output, wherein the one or more instructions comprise an instruction to change the operation of the control system of a second portable detector that is associated with a second candidate sample of the plurality of portable detectors, and wherein the second portable detector is distinct from the first portable detector.

2. The portable genetic detector system of claim 1, wherein the at least one analysis output comprises an assembly of the sample data identifying the nucleotides present in the biological sample.

3. The portable genetic detector system of claim 2, wherein the at least one analysis output comprises an indication that the assembly represents a predetermined sequence coverage for a region of a genome of interest for the first portable detector of the plurality of portable detectors.

4. The portable genetic detector system of claim 3, wherein the one or more instructions comprise an additional instruction to stop operation of the reader of the biological sample for the first portable detector when the assembly represents the predetermined sequence coverage.

5. The portable genetic detector system of claim 3, wherein the one or more instructions comprise an additional instruction to stop operation of the reader of each of the portable detectors when the assembly represents the predetermined sequence coverage.

6. The portable genetic detector system of claim 2, wherein the processor is configured to analyze the sample data from each of the portable detectors to determine that the biological sample of one or more of the plurality of portable detectors matches a signature from a group of predefined signatures.

7. The portable genetic detector system of claim 6, wherein the one or more instructions comprise a halt instruction that causes the control system to stop operation of the reader of each of the portable detectors when the biological sample of one or more of the portable detectors matches the signature from the group.

8. The portable genetic detector system of claim 2, wherein the at least one analysis output comprises an indication of data quality for the sample data collected by the reader for each of the portable detectors.

9. The portable genetic detector system of claim 8, wherein the one or more instructions comprise an additional instruction to stop operation of the reader of the second portable detector when a predetermined data quality score is achieved.

10. The portable genetic detector system of claim 1, wherein the sequencing assembly data comprises assembly of the identified nucleotides from individual nucleotide sequence segments to generate one or more longer nucleotide sequence segments.

11. The portable genetic detector system of claim 1, wherein the housing of the respective portable genetic detector is configured to receive a removable interface distinct from the interface or processing device.

12. The portable genetic detector system of claim 1, wherein the processor analyzing the sample data comprises the processor assembling a sequence of nucleotides based on the identified nucleotides, and wherein the sequencing assembly data is the sequence of nucleotides.

13. The portable genetic detector system of claim 1, wherein the processor is programmed to determine location data associated with the biological sample corresponding to the first candidate sample and cause the communications circuitry to provide the instructions to change the operation of the control system of the second portable detector based on the location data.

* * * * *

UNITED STATES PATENT AND TRADEMARK OFFICE
CERTIFICATE OF CORRECTION

| | | |
|---|---|---|
| PATENT NO. | : 11,634,746 B2 | Page 1 of 1 |
| APPLICATION NO. | : 16/540769 | |
| DATED | : April 25, 2023 | |
| INVENTOR(S) | : Kain et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 359 days.

Signed and Sealed this
Twelfth Day of November, 2024

Katherine Kelly Vidal
*Director of the United States Patent and Trademark Office*